(12) United States Patent
Gunstream et al.

(10) Patent No.: US 7,435,602 B2
(45) Date of Patent: Oct. 14, 2008

(54) REDUCING EFFECTS OF SPECTRAL NONUNIFORMITY

(75) Inventors: Stephen J. Gunstream, San Francisco, CA (US); Mark F. Oldham, Los Gatos, CA (US); Michael R. Gambini, Bolton, MA (US); John C. Voyta, Sudbury, MA (US)

(73) Assignee: Applied Biosystems Inc., Foster City, CA (US)

( * ) Notice: Subject to any disclaimer, the term of this patent is extended or adjusted under 35 U.S.C. 154(b) by 931 days.

(21) Appl. No.: 10/757,903

(22) Filed: Jan. 14, 2004

(65) Prior Publication Data
US 2004/0259260 A1 Dec. 23, 2004

Related U.S. Application Data

(63) Continuation-in-part of application No. 10/323,669, filed on Dec. 20, 2002, now abandoned.

(51) Int. Cl.
*G01N 21/64* (2006.01)
*G01N 35/00* (2006.01)

(52) U.S. Cl. ............... 436/172; 422/67; 422/82.08; 436/8; 436/43; 436/47; 436/94; 702/19; 702/22

(58) Field of Classification Search ............. 422/63–67, 422/82.05, 82.08–82.09; 436/43, 46–47, 436/94, 172, 8; 702/19–20, 22, 27–28
See application file for complete search history.

(56) References Cited

U.S. PATENT DOCUMENTS

| | | | | |
|---|---|---|---|---|
| 5,766,875 | A * | 6/1998 | Hafeman et al. | 435/29 |
| 5,854,684 | A * | 12/1998 | Stabile et al. | 356/440 |
| 5,861,256 | A * | 1/1999 | Glass et al. | 435/6 |
| 6,348,965 | B1 * | 2/2002 | Palladino et al. | 356/243.1 |
| 6,441,973 | B1 * | 8/2002 | Ramm et al. | 359/778 |
| 6,518,068 | B1 * | 2/2003 | Gambini et al. | 436/50 |
| 2002/0070349 | A1 * | 6/2002 | Hoyt | 250/458.1 |

FOREIGN PATENT DOCUMENTS

WO WO 01/06238 A2 1/2001
WO WO 02/086416 A2 10/2002

OTHER PUBLICATIONS

Chapman, G. B., II et al, Applied Spectroscopy 1978, 32, 46-53.*
Harrison, R. O. et al, Journal of the Association of Official Analytical Chemists 1988, 71, 981-987.*
Vesanen, M. et al, Journal of Virological Methods 1996, 59, 1-11.*
Escobar, N. I. et al, Journal of Immunological Methods 1996, 196, 97-99.*
Ray, K. G. et al, Applied Spectroscopy 1997, 51, 108-116.*

(Continued)

*Primary Examiner*—Arlen Soderquist

(57) ABSTRACT

Method and system providing calibration of light detected from biological samples with a correction factor including components for each of a plurality of spectrally distinguishable species and/or for each well and/or for each filter.

20 Claims, 15 Drawing Sheets

OTHER PUBLICATIONS

Grundmann, H. J. et al, Journal of Clinical Microbiology 1997, 35, 3071-3077.*

Liu, Y. et al, Analytical Biochemistry 1999, 267, 331-335.*

Lin, K. et al, BioTechniques 1999, 26, 318-320, 322, 324-326.*

Abriola, L. et al, Journal of Biomolecular Screening 1999, 4, 121-127.*

Bantan-Polak, T. et al, Analytical Biochemistry 2001, 297, 128-136.*

Colantuoni, C. et al, Bio Techniques 2002, 32, 1316-1320.*

Fowler et al., A Multi-Modality Assay Platform For Ultra-High Throughput Screening, Current Pharmaceutical Biotechnology, 2000, vol. 1, No. 3, pp. 265-281.

* cited by examiner

REDUCING EFFECTS OF SPECTRAL NONUNIFORMITY

PRIORITY

This application claims the benefit as a continuation-in-part from U.S. Ser. No. 10/323,669, filed on Dec. 20, 2002, now abandoned, that claimed priority to U.S. Ser. No. 09/621,961, filed on Jul. 21, 2000 (issued as U.S. Pat. No. 6,518,068 B1 on Feb. 11, 2003), that claimed priority to U.S. Provisional Application Ser. No. 60/144,891, filed on Jul. 21, 1999.

FIELD

The present teachings relate to apparatuses and methods for spectral calibration, and more particularly to reducing the effects of spectral non-uniformity detected from a biological sample including multiple spectrally distinguishable species.

BACKGROUND

Real-time detection of DNA amplification during the polymerase chain reaction (PCR) process provides quantitative data for amplifiable DNA target sequences by relating the number of temperature cycles during thermal cycling to reach a concentration threshold (Ct) of the target sequence to the amount of target DNA present at the beginning of the PCR process. The determination of the amount of target DNA present can be effected by detecting the accurate Ct.

High-throughput systems can provide DNA amplification of multiple samples in parallel, such as in a microwell tray or microcard. Assays can provide multiple DNA target sequences of interest, such as diagnostic assays for HIV screening. These assays can provide multiple spectrally distinguishable species, such as different fluorescent dyes, to detect Ct values for each of the multiple DNA target sequences of interest in each of the multiple samples thermally cycled in parallel.

Spectral non-uniformity between multiple samples thermally cycled in parallel at different locations on the tray and/or multiple dyes at the same location on the tray can cause repeatable systematic Ct error. Spectral non-uniformity can result from spectral variation in excitation light provided to the samples, spectral variations due to optical components, such as filters and beam splitters, and/or spectral variations in the detector. It can be desirable to reduce the effects of spectral non-uniformity between the multiple samples thermally cycled in parallel by calibrating the detection of light from the biological samples by determining a correction factor to more accurately detect Ct values.

SUMMARY

According to various embodiments, the present teachings provide a method for calibrating detection of light from biological samples including providing a system adapted to excitation and detection of a plurality of spectrally distinguishable species, wherein the system includes a plurality of filters providing a calibration plate including a plurality of wells, wherein each well includes a sample with a spectrally distinguishable species detecting light from the spectrally distinguishable species for each well determining a correction factor for each spectrally distinguishable species for each well.

According to various embodiments, the present teachings provide a method for calibrating detection of light from biological samples including providing a system adapted to excitation and detection of a plurality of spectrally distinguishable species, wherein the system includes a plurality of filters providing a calibration plate including a plurality of wells, wherein each well includes a sample with a spectrally distinguishable species detecting light from each filter for each well determining a correction factor for each filter.

According to various embodiments, the present teachings provide a system for detection of light from biological samples, the system including a detector a plurality of filters a plurality of spectrally distinguishable species and a plurality of wells, wherein the detector is adapted to determine a correction factor for each spectrally distinguishable species, for each filter, for each well.

According to various embodiments, the present teachings provide a computer-readable software including code adapted to calibrate detection of light from a biological sample, the code providing commands including determining a correction factor for each of a plurality of spectrally distinguishable species in the biological sample, wherein determining includes (1) generating a set of simultaneous equations for image data detected from each of the spectrally distinguishable species, and (2) solving the set of simultaneous equations for a contribution to the correction factor of each of the spectrally distinguishable species and normalizing the image data detected from the biological sample.

According to various embodiments, the present teachings provide a system for detection of light from biological samples, the system including means for detecting the light from the biological samples means for filtering the light from a plurality of spectrally distinguishable species, wherein the filtering is adapted to each spectrally distinguishable species means of containing an array of biological samples, wherein the light from each sample provides a different angle to the means for detecting and means for determining a correction factor for each spectrally distinguishable species, wherein the correction factor has components for filtering and containing.

According to various embodiments, the present teachings provide a calibration plate for detection of light from biological samples, the plate including a plurality of wells a plurality of samples and a spectrally distinguishable species, wherein each well includes a sample, wherein each sample includes a spectrally distinguishable species, wherein each well is adapted to provide a correction factor for a plurality of filters.

According to various embodiments, the present teachings provide a calibration plate for detection of light from biological samples, the plate including a substrate including a plurality of locations, wherein each location is adapted to provide light representing a plurality of spectrally distinguishable species to determine a correction factor for a plurality of filters for each location.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description herein and appended claims.

Figure 1:
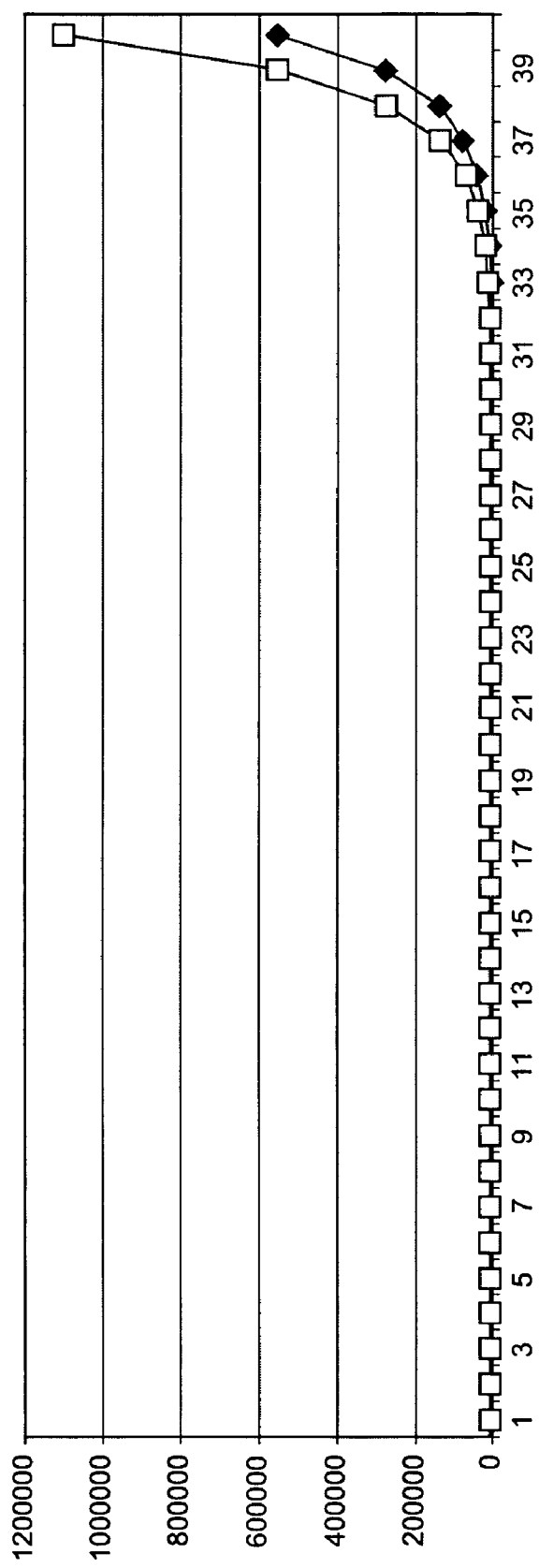
FIG. 1 illustrates Ct error by showing a plot of concentration versus cycles for two exemplary runs of the same dye.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

It is to be understood that both the foregoing general description and the following detailed description are exemplary and explanatory only, and are intended to provide an explanation of various embodiments of the present teachings.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

DESCRIPTION OF VARIOUS EMBODIMENTS

Reference will now be made to various exemplary embodiments, examples of which may be illustrated in the accompanying drawings. Wherever possible, the same reference numbers are used in the drawings and the description to refer to the same or like parts.

The term "detector" as used herein refers to a charge coupled device (CCD), a charge induction device (CID), an array of photomultiplier tubes (PMT), Photodiode, CMOS device, and other means of detecting fluorescent light emitted from the multiple spectrally distinguishable species in the sample. The detector can include an external computer or internal processor that provides calculation to determine correction factors. The term "spectrally distinguishable species" as used herein refers to dyes, reporters, or reagents such as FAM, SYBR Green, VIC, JOE, TAMRA, NED, CY-3, Texas Red, CY-5, ROX (passive reference), etc. The term "filter" as used herein refers optical filters in visible or near-visible range such as infra-red, gratings, prisms and other optical components that can be influenced by angle of incidence.

According to various embodiments, the present teachings include a calibration plate for each spectrally distinguishable species. Prior to the real multiplexed (multiple reagent) samples, standards containing only a single reagent in each well are imaged and analyzed. These standards will produce a set of coefficients to be used collectively as multi-component coefficients for each optical filter, for each well. For a given optical filter, the target reagent for that filter should produce the highest output. The other reagents may also have spectra in the filter's bandpass, and will produce smaller outputs, which are a measure of the overlap of those nontarget reagent spectra into the filter signal. For example, the filter's output for the target reagent might be 850, and the filters output for the other 2 reagents might be 100 and 50, respectively. If the 3 reagents were added together in a single well, the total output would be 1000, and the proportions would be 850:100:50. These coefficients are measured for each well location and filter separately, which gives a complete set of coefficients for simultaneous equations. This will allow a solution for any combination of concentrations of reagent in one sample well. Further in the preferred embodiment, these coefficients will also be normalized by the total intensity read in the "total emission" filter, so that the calculation will result in the same intensity as the instrument would measure if only a single reagent was measured by the "total emission" filter. This calculation may be shown as follows for a simple case of blue and green reagents (abbreviated as R in the calculations), and blue and green and total emission filters (abbreviated as F in the calculations):

Let A=(output of the instrument for blue R thru the blue F)/(output of instrument for blue R thru total emission F);

Let B=(output of the instrument for green R thru the blue F)/(output of instrument for green R thru total emission F);

Let C=(output of the instrument for blue R thru the green F)/(output of instrument for blue R thru total emission F);

Let D=(output of the instrument for green R thru the green F)/(output of instrument for green R thru total emission F);

These coefficients are measured for each well prior to running a multi-color run. Then for a multi-reagent/color run, (output of the instrument for the blue F)=A×(true intensity of blue R)+B×(intensity of green R);

and (output of the instrument for the green F)=C×(true intensity of blue R)+D×(intensity of green R)

These 2 simultaneous equations are then solved for the true intensity of the blue and green reagents by the processing software.

According to various embodiments, present teachings include a calibration plate for each spectrally distinguishable species. According to various embodiments, the Ct error is equal to $\log_2(a_i)$, where $a_i$ is the ratio of (reporter$_i$)/(reporter$_{average}$). According to various embodiments, if an internal reference is used the Ct error is equal to $\log_2(a_i)$, where $a_i$ is the ratio of (reporter$_i$/internal reference$_i$)/(reporter$_{average}$/internal reference$_{average}$). FIG. 1 illustrates the effect of a two-fold difference in the reporter to internal reference ratio by plotting concentration versus number of cycles to show the Ct error between two sets of values.

According to various embodiments, the correction factors or coefficients can be used to correct the ratio for a pair of dyes, where one of the dyes in each case is the internal reference by correcting the spectral non-uniformity post-normalization. According to various embodiments, the intensity response can be normalized for each dye on an absolute basis by correcting the spectral non-uniformity prior to normalization. Correction prior to normalization can provide correction for a system using an internal reference or a system that does not use an internal reference.

According to various embodiments, errors in the internal reference background can provide Ct errors by creating an incorrect offset that is not subtracted. The offset can be reduced by baseline correcting the Ct data. The background error is equal to $\log_2(b_i)$, where $b_i$ is the ratio of (internal reference$_i$+internal reference background$_i$)/internal reference$_i$. Background can come from several sources, including camera dark current, stray light within the optical system, light leakage into the optical system, intrinsic fluorescence of the tray, tray seal, filters, beam splitters, lenses, or other optical components. It can also come from various sources of contamination within the system, such as dust, spills within the wells, or insufficient blocking of excitation light. Offset typically comes from the camera, but can also be introduced by other electronics, or by firmware or software.

Figure 2:
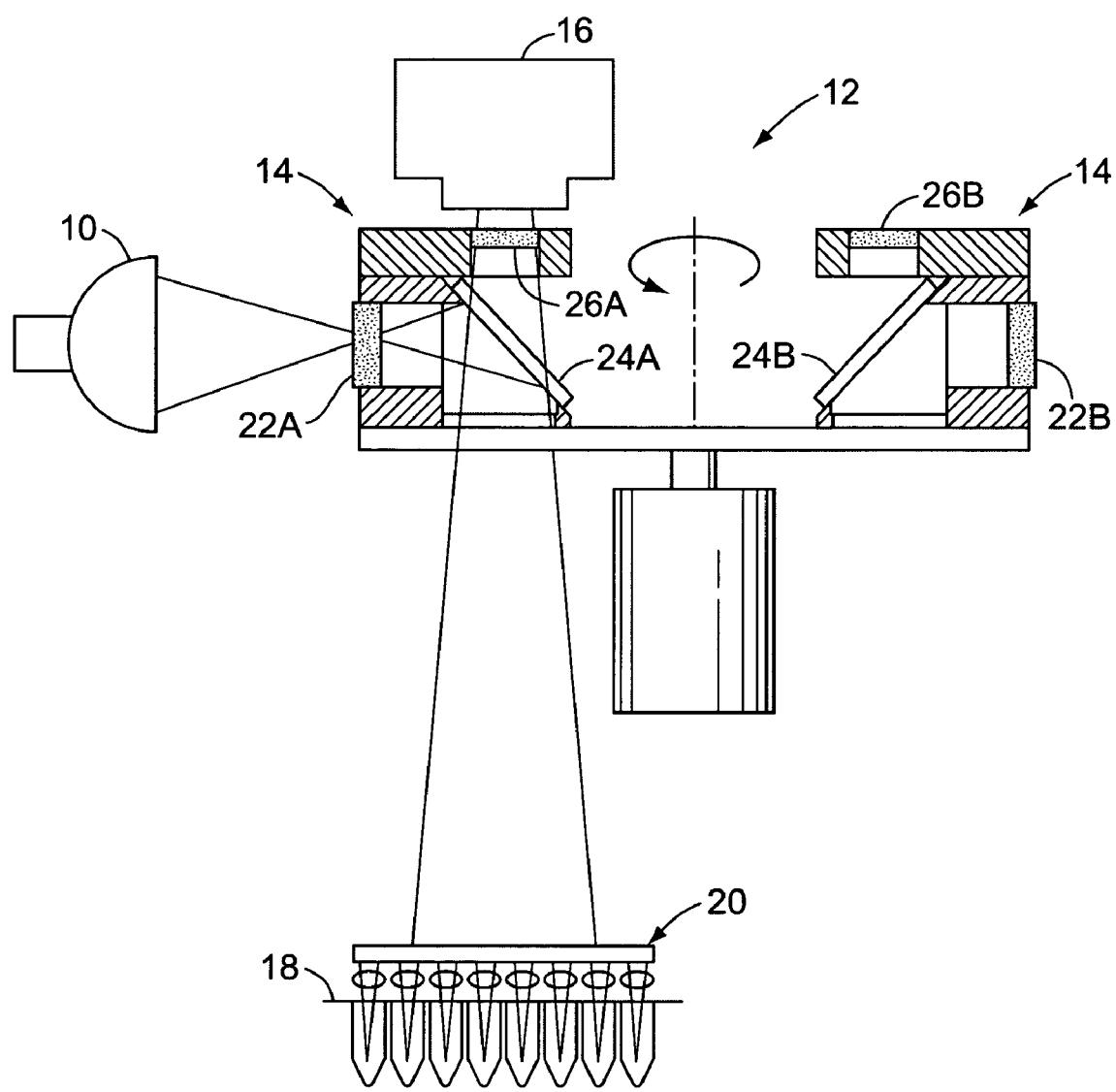
FIG. 2 illustrates an exemplary configuration for a system for detection providing Ct error.

According to various embodiments, FIG. 2 illustrates an exemplary system for detection. The system can include light source 10, filter turret 12 with multiple filter cubes 14, detector 16, microwell tray 18, and well optics 20. Each filter cube 14 can include an excitation filter 22, a beam-splitter 24, and an emission filter 26. These can be each provided to correspond to one of the multiple spectrally distinguishable species such that species A can correspond to the filter cube 14 with excitation filter 22A, beam-splitter 24A, and emission filter 26A, species B can correspond to the filter cube 14 with excitation filter 22B, beam-splitter 24B, and emission filter 26B, and so on for other species that can be detected from the samples in microwell tray 18. It will be apparent to one skilled in the art that other systems with different configurations will provide spectral non-uniformity since optical filters are interference devices, their bandpass characteristics vary, dependent on the angle of incidence of the emission to be filtered. The angle of incidence will be unique for each well because each well's specific location is unique relative to the optical filter. Accordingly, all calculations and filter coefficients are unique per sample well. It will be apparent to one skilled in the art that other systems for detection with different components, for example without a filter turret, will benefit from the present teachings.

According to various embodiments, corrections for spectral non-uniformity can be provided to raw fluorescence data. According to various embodiments, corrections for spectral non-uniformity can be provided during Ct data processing. The data processing can include multi-component analysis for the different spectrally distinguishable species that provides calculating separately the concentration of each species in the samples that can contain multiple species. According to various embodiments, corrections for spectral non-uniformity can be provided in a post-processing step. According to various embodiments, the raw data can be retained in addition to a second corrected set. This can provide access to the raw data so that the effects of the correction can be observed while insuring that all visualizations of the data are consistent with the corrections. According to various embodiments, the present teachings provide custom application software for correction of raw data, during data processing, and/or post-processing. According to various embodiments, the post-processing step can be provided in a spreadsheet or other calculation software that can capture the raw data and provide the corrections for spectral non-uniformity.

According to various embodiments, spectral non-uniformity can be reduced by providing non-normalized calibration matrices for each of the spectrally distinguishable species. Normalized matrices can be baseline corrected by identifying the local signal maximum through filling one particular well in a given plate with high intensity species, imaging the plate, and analyzing all of the wells in the plate for their response to the one high intensity species well. The baseline is collected for all the wells individually by repeating the process for every different well location desired for the complete data set which can include interpolation for larger plate, i.e., 384-well plate with 96-area baseline. The baseline can be applied by normalizing all the wells to the well with the highest intensity. According to various embodiments, non-normalized matrices provide correction factors for each spectrally distinguishable species for each well.

According to various embodiments, multiwell trays can be heat sealed with an adhesive film during normal operation and calibration. The adhesive film can provide variation in the transmission of light from well-to-well for the multiwell trays during calibration, due to uneven melting and optical effects from the adhesive film. In such embodiments, non-normalized matrices can be difficult to determine. The adhesive film used during normal operation reduces the optical effects and provides uniform well-to-well optical transmission through the film. The adhesive film used during calibration increases evaporation, may decrease the accuracy of the calibration, and decreases the useful life of the calibration tray for generating accurate correction factors.

According to various embodiments, spectral non-uniformity can be determined by using the plateau in the Ct values at the end of the thermal cycling process. According to various embodiments, the plateau method can normalize using the value of the final cycle. This normalization can be performed relative to the maximum value, the minimum value, or the average (that can remove outlying values). A normalization factor is determined for each well, for each spectrally distinguishable species. This can be done either for an assay with an internal reference, or an assay without an internal reference. All values within the assay are then multiplied by the normalization factor at each cycle, for each dye. According to various embodiments, the plateau method can normalize using the average value from several cycles at the end of the run. According to various embodiments, the plateau method can normalize using all the values within a constant of the final cycle. According to various embodiments, the Ct values may not reach a plateau in some cases such that the correction for spectral non-uniformity may not be determined. Some of the cases where the assay does not reach a plateau include assays with no template controls, assays that are not optimized properly due to reagents or temperature controls, assays that are run for an insufficient number of cycles for the amplification to reach the plateau, assays with multiple spectrally distinguishable species where there is competition for some of the components of the reaction.

According to various embodiments, spectral non-uniformity can be determined by using Ct values from an unquenched reporter dye during the beginning cycles of the thermal cycling process. Similar to the plateau method, data from the beginning of the assay can be used to compensate for the spectral non-uniformity. According to various embodiments, there are a number of cycles prior to measurable amplification. For example, at least fifteen cycles can elapse prior to measurable amplification. The signal level prior to measurable amplification is lower than the signal level at the end of the run. Maximizing the number of cycles prior to measurable amplification for the basis of the average can provide an accurate correction value similar to the plateau method. According to various embodiments, assays may quench the spectrally distinguishable species such that there is poor signal to noise to determine the correction for spectral non-uniformity. According to various embodiments, molecular beacons provide such quenching when the quencher and probe emitter are held close to each other via a hairpin structure in the single stranded state of the probe, and a linear probe where the quencher is on a separate short oligo complementary to the probe, where the quencher and probe emitter are hybridized. The quencher and probe are in close proximity to each other at the low temperatures during the extension phase and hold phase of the thermal cycle.

Figure 3:
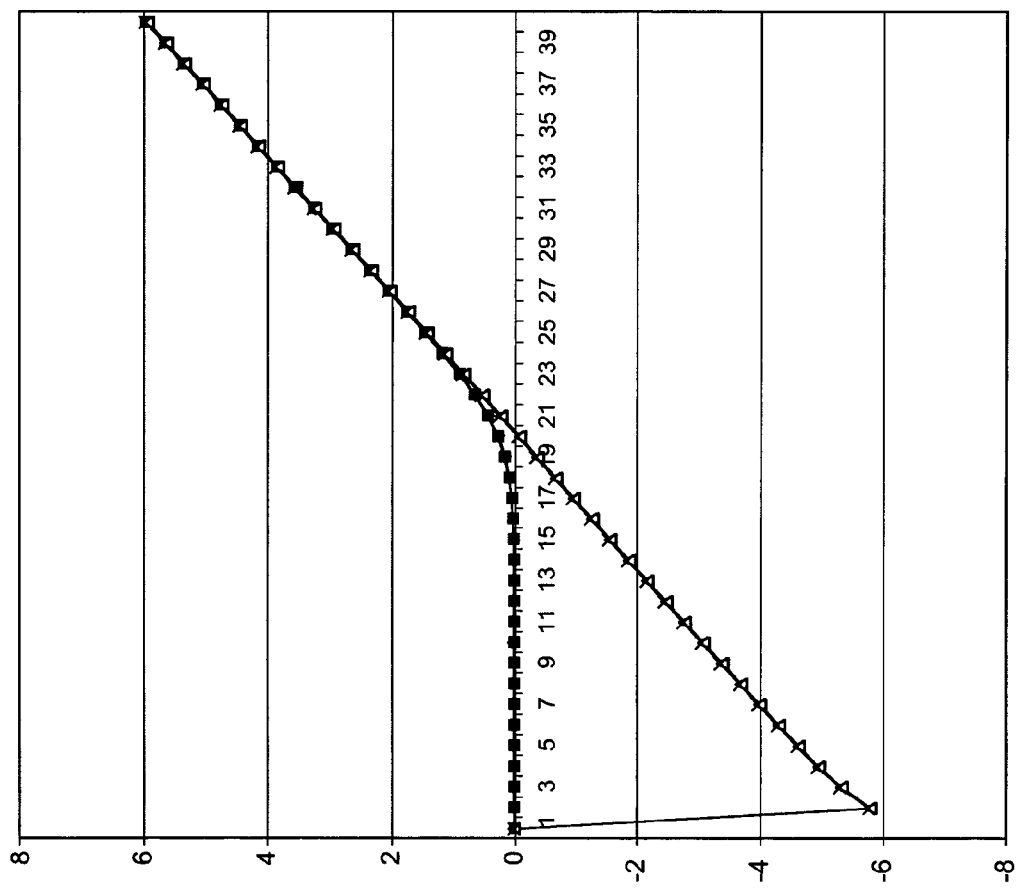
FIG. 3 illustrates the effect of variations in background and unquenched dye by showing a log-linear plot of ratio of reporter dye to reference versus cycles for four exemplary runs of the same dye.

According to various embodiments, spectral non-uniformity can be removed by determining Ct values from log-log plots of concentration versus cycles. In log-log plots, the effect of spectral non-uniformity on Ct values can be removed, but the log-log plots are sensitive to variations in background and variations in the amount of unquenched probe. According to various embodiments, log-log plots can include reporter dye concentration. According to various embodiments, log-log plots can include the ratio of reporter dye concentration and internal reference dye concentration. According to various embodiments, log-log and/or log-linear plots may be affected by variations in background and unquenched dye as illustrated in FIG. 3.

According to various embodiments, spectral non-uniformity can be determined by using a calibration plate. According to various embodiments, the calibration plate can be a multiwell calibration tray with multiple dyes in each well of the tray. According to various embodiments, the calibration plate can be a solid plate constructed of and/or coated with material such as capable of providing calibration wavelengths of reflected or fluorescent light to determine the correction factor to compensate for spectral non-uniformity. According to various embodiments, a substrate including a plurality of locations that represent the wells in tray can be constructed such that each location is adapted to provide light representing the plurality of spectrally distinguishable species in the sample to determine a correction factor for each of the plurality of filters for each location that will be used as a correction factor for each well represented by the location. According to various embodiments, two thin solid plates where one part of the spectra can be provided by one plate and the second part of the spectra by the other plate.

According to various embodiments, each of the spectrally distinguishable species, i.e. dyes, can be deconvolved to determine a correction factor for each dye for each well. According to various embodiments, the dyes may be less spectrally distinguishable, i.e. TAM and NED dyes, so that it may be difficult to determine the correction factors to by using a single calibration plate. Dyes that are less spectrally distinguishable from each other spectrally can require multiple calibration plates. According to various embodiments, multiple calibration plates can lead to the user of detection system to associate each dye with a particular filter so that the correction factors for spectral non-uniformity can provide the intended effect on accuracy of Ct values.

According to various embodiments, spectral non-uniformity can be determined by using a calibration plate to provide correction factors for the multiple filters. According to various embodiments, the calibration plate for filters can include dyes that are more spectrally distinguishable and so that each dye is closely matched with a single filter channel in the detection system. According to various embodiments, the spectral calibration can be performed on a filter-to-filter basis, as opposed to a dye-to-dye basis. The association of filters with dyes no longer needed.

According to various embodiments, the filter-based correction factors for spectral non-uniformity can be applied at any point during analysis. According to various embodiments, the filter-based correction factors can be applied to the pure dye normalized calibration matrices. According to various embodiments, the filter-based correction factors can be applied to the raw data after offset and background subtraction, but prior to any display of data, so that display of data is self consistent, and consistent with the final results. According to various embodiments, correction of the internal control background variation can include subtracting the buffer background used in creating the pure dye normalized calibration matrices from the raw data before dye deconvolution or spectral non-uniformity correction.

EXAMPLES

Figure 4A:
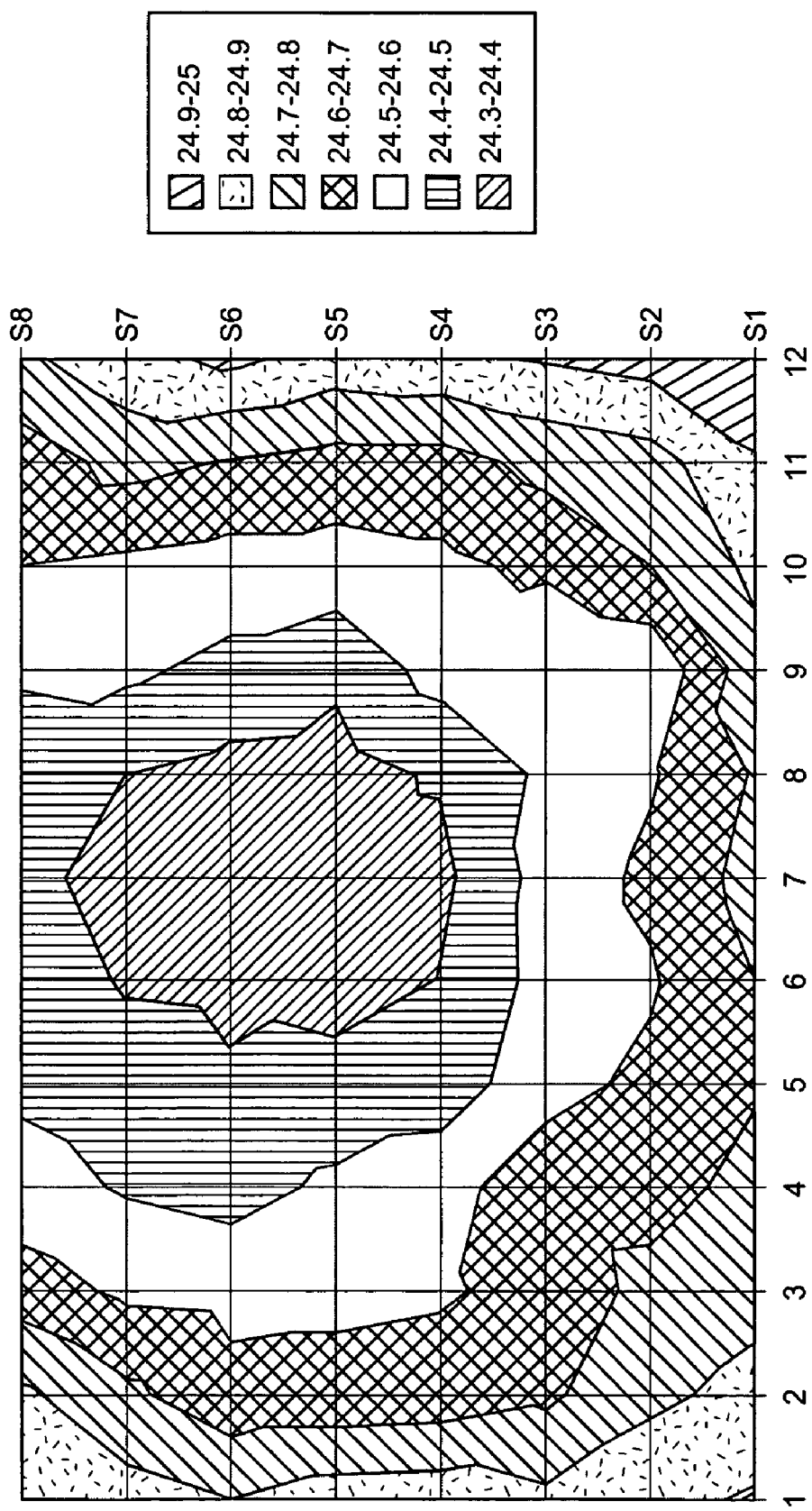
FIGS. 4A-4F illustrate an example using FAM dye with ROX as reference to show effect of correction factor on Ct values according to various embodiments of the present teachings.
Figure 4B:
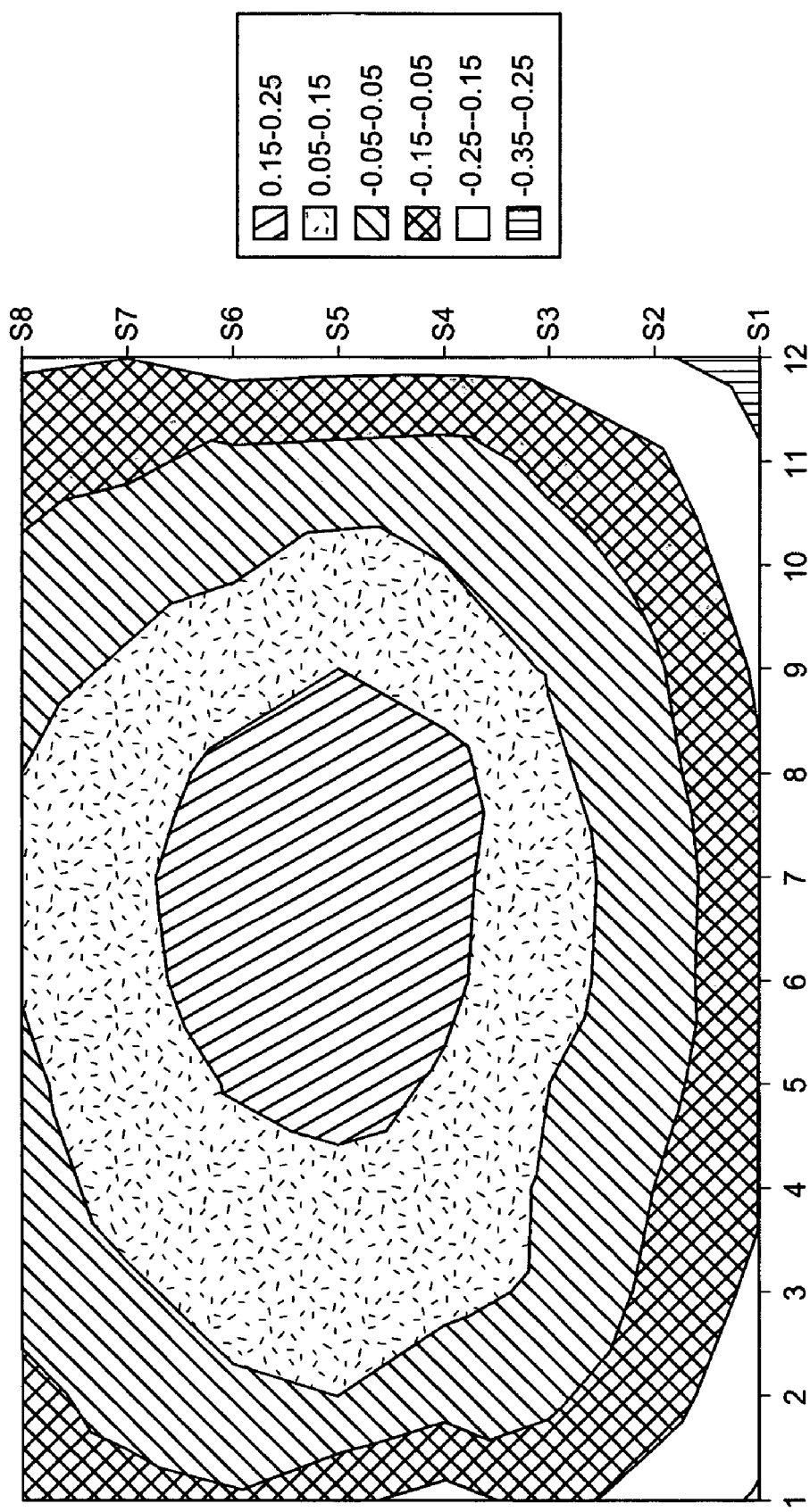
Figure 4C:
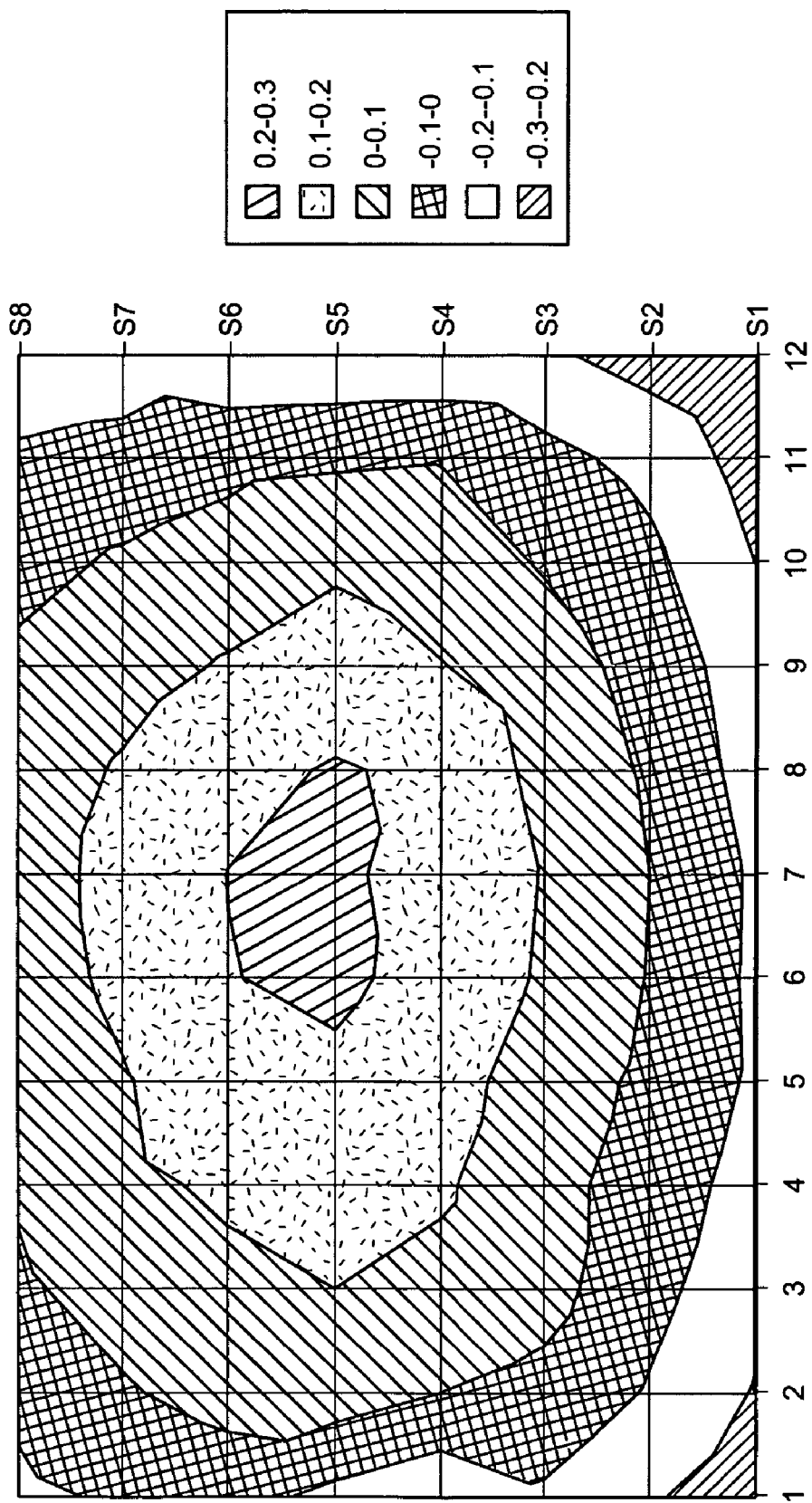
Figure 4D:
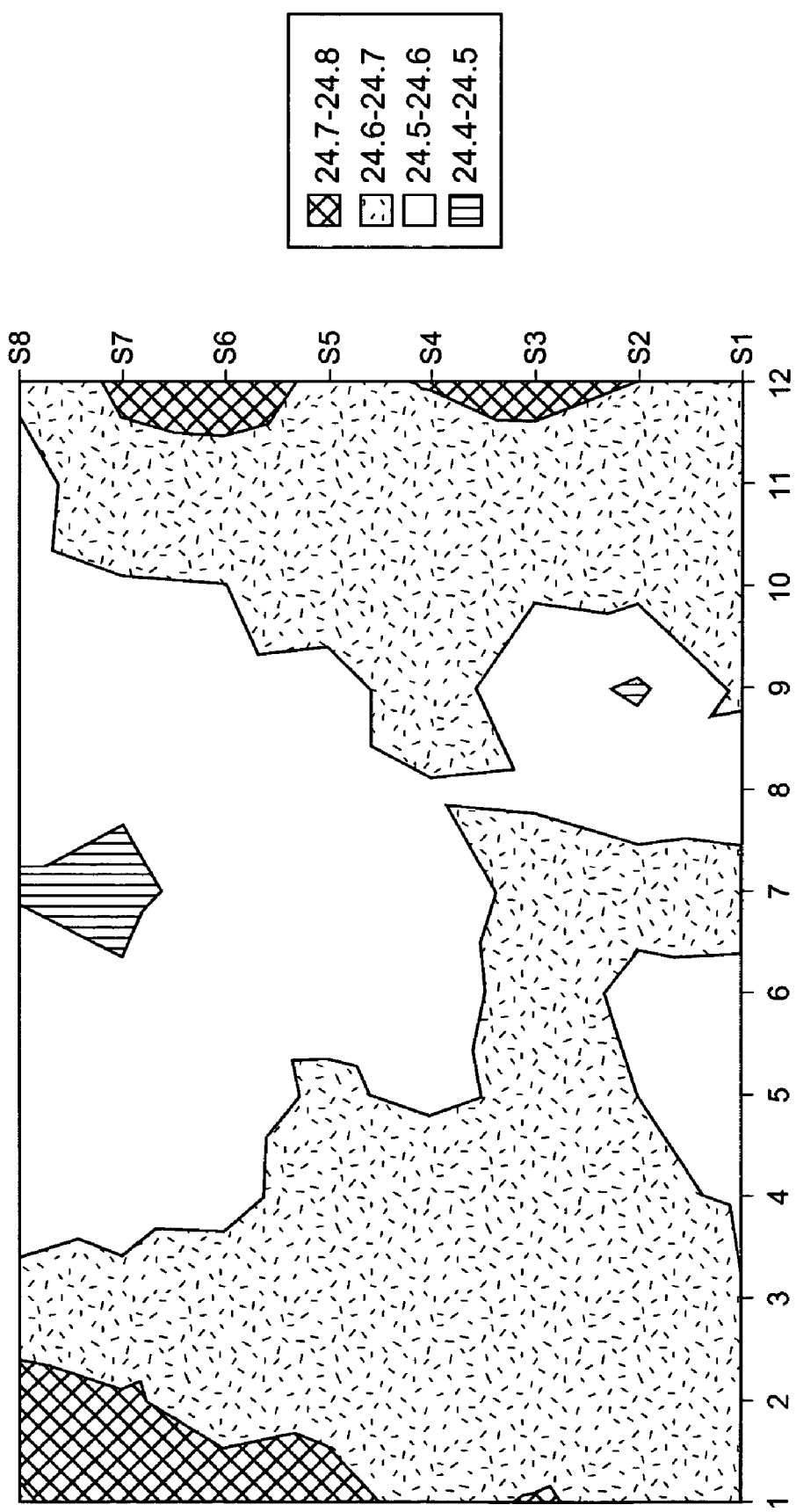
Figure 4E:
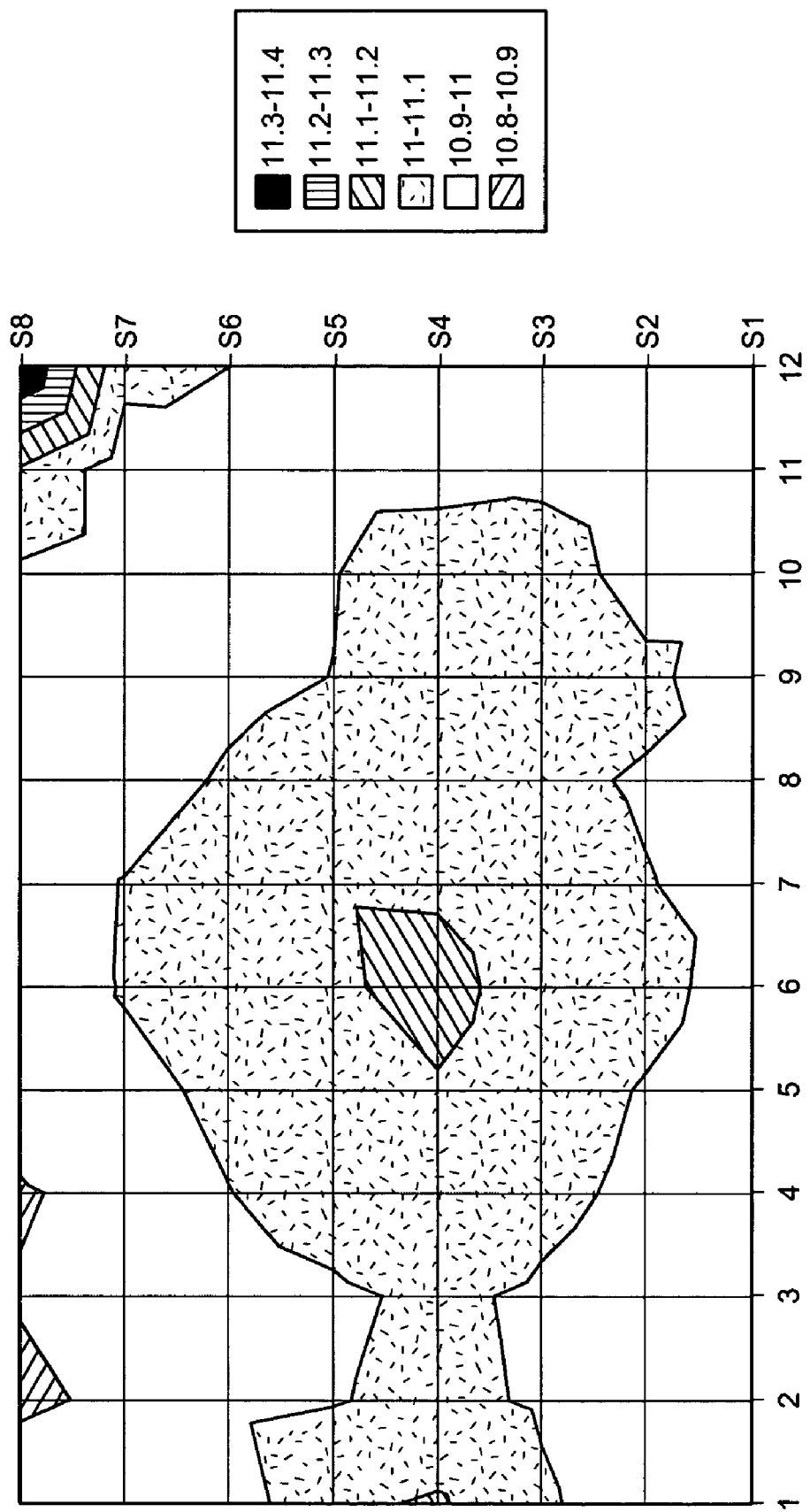
Figure 4F:
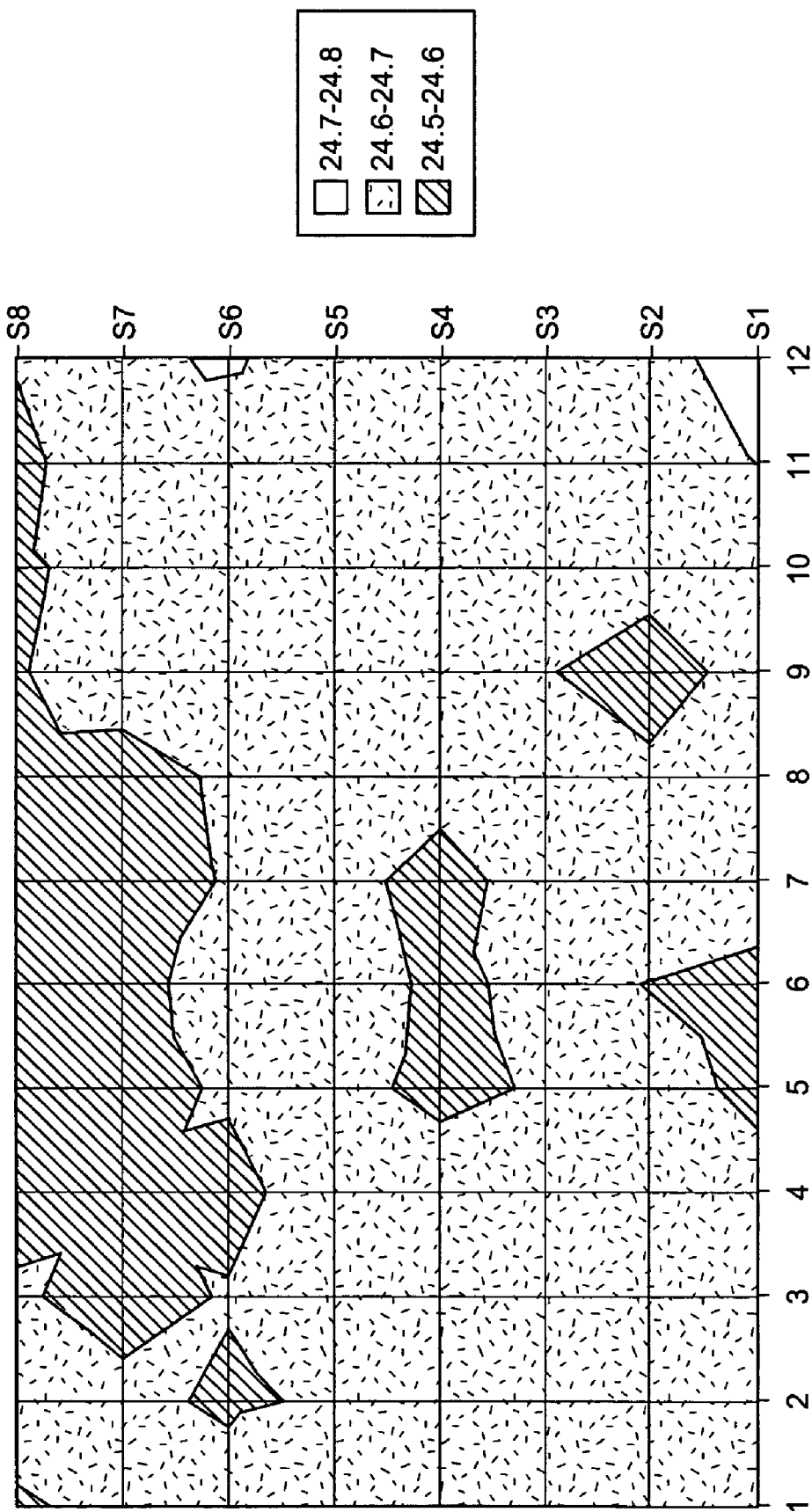
Figure 5A:
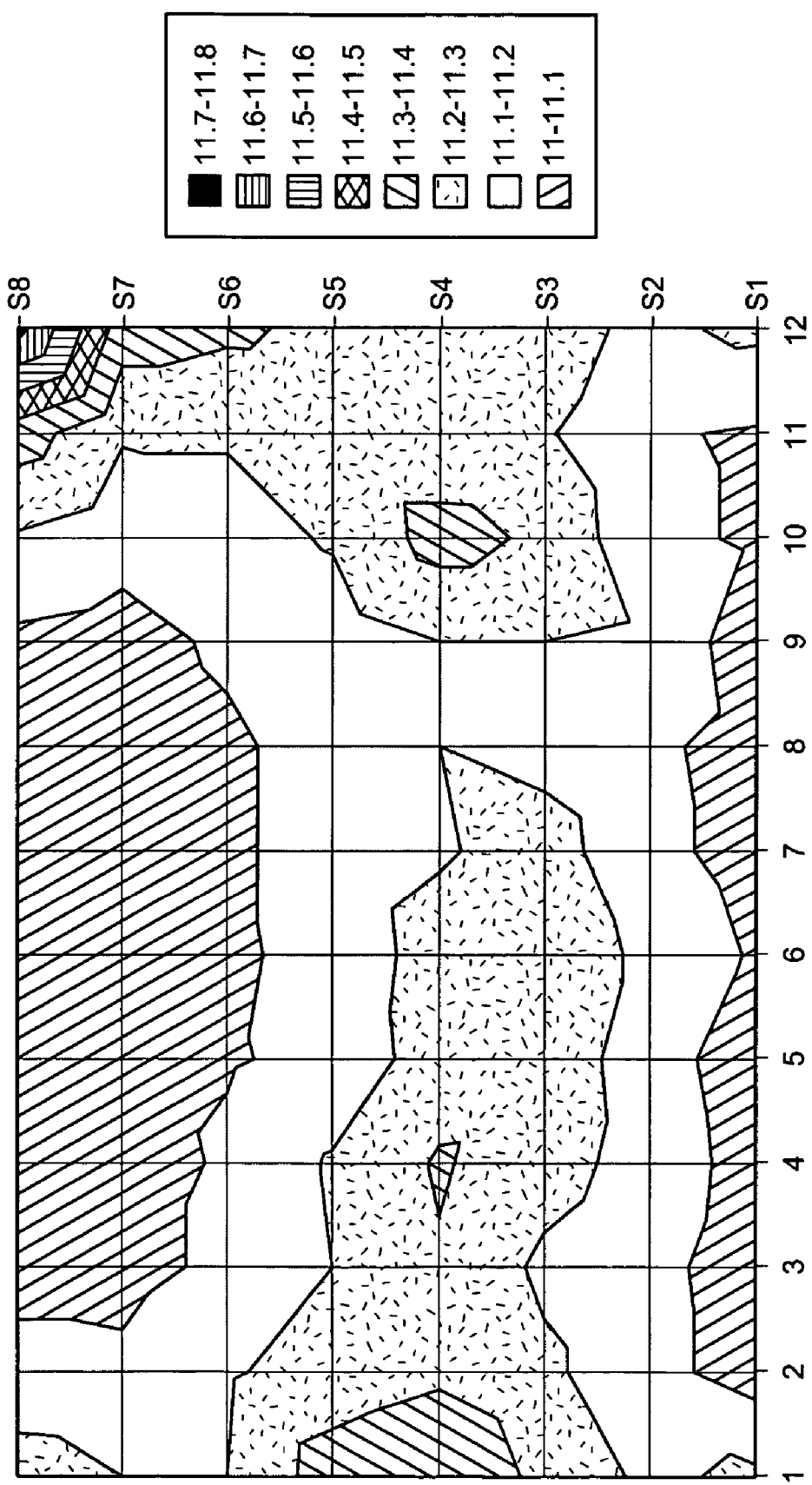
FIGS. 5A-5F illustrate an example using VIC dye with ROX as reference to show effect of correction factor on Ct values according to various embodiments of the present teachings.
Figure 5B:
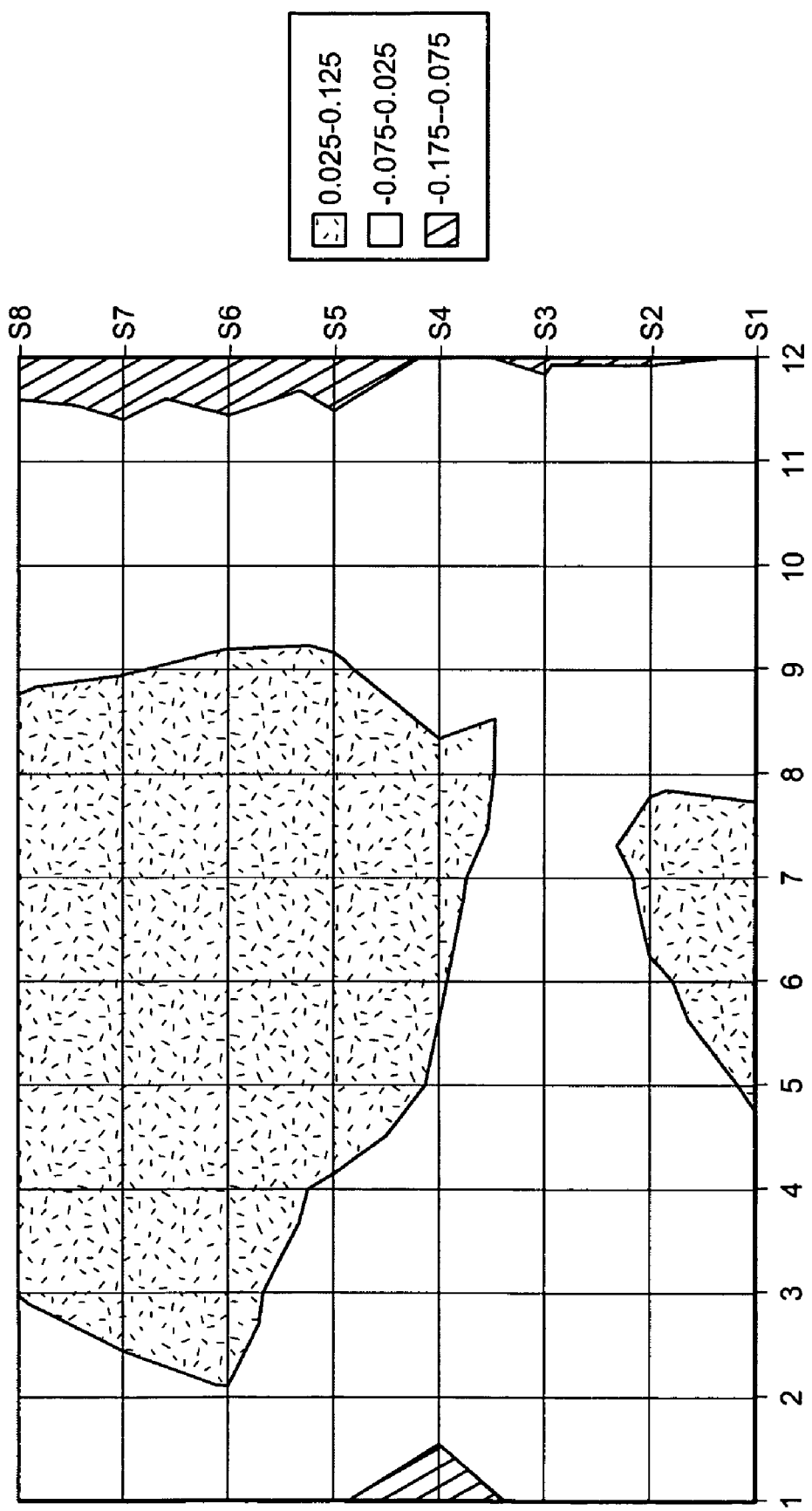
Figure 5C:
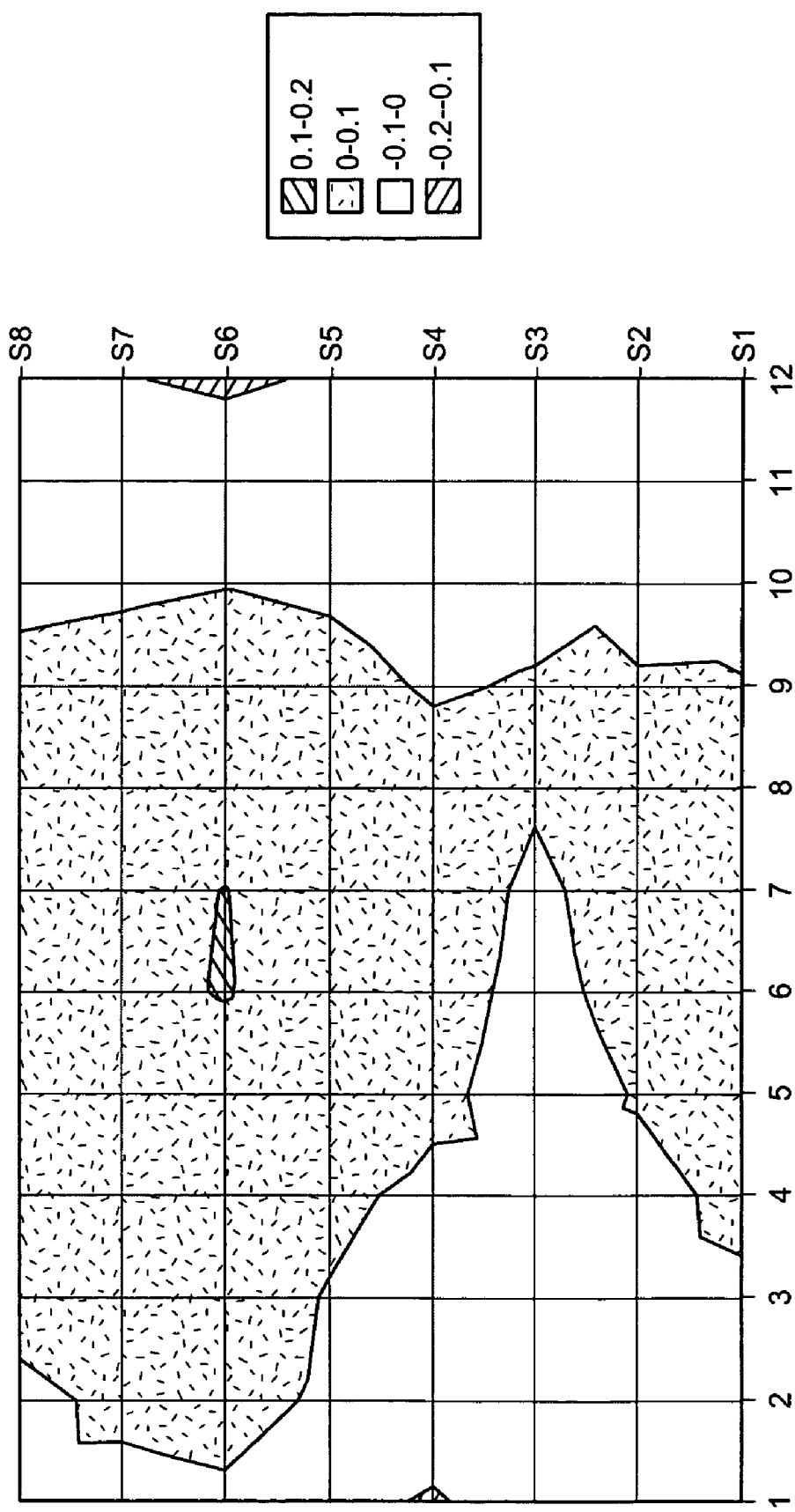
Figure 5D:
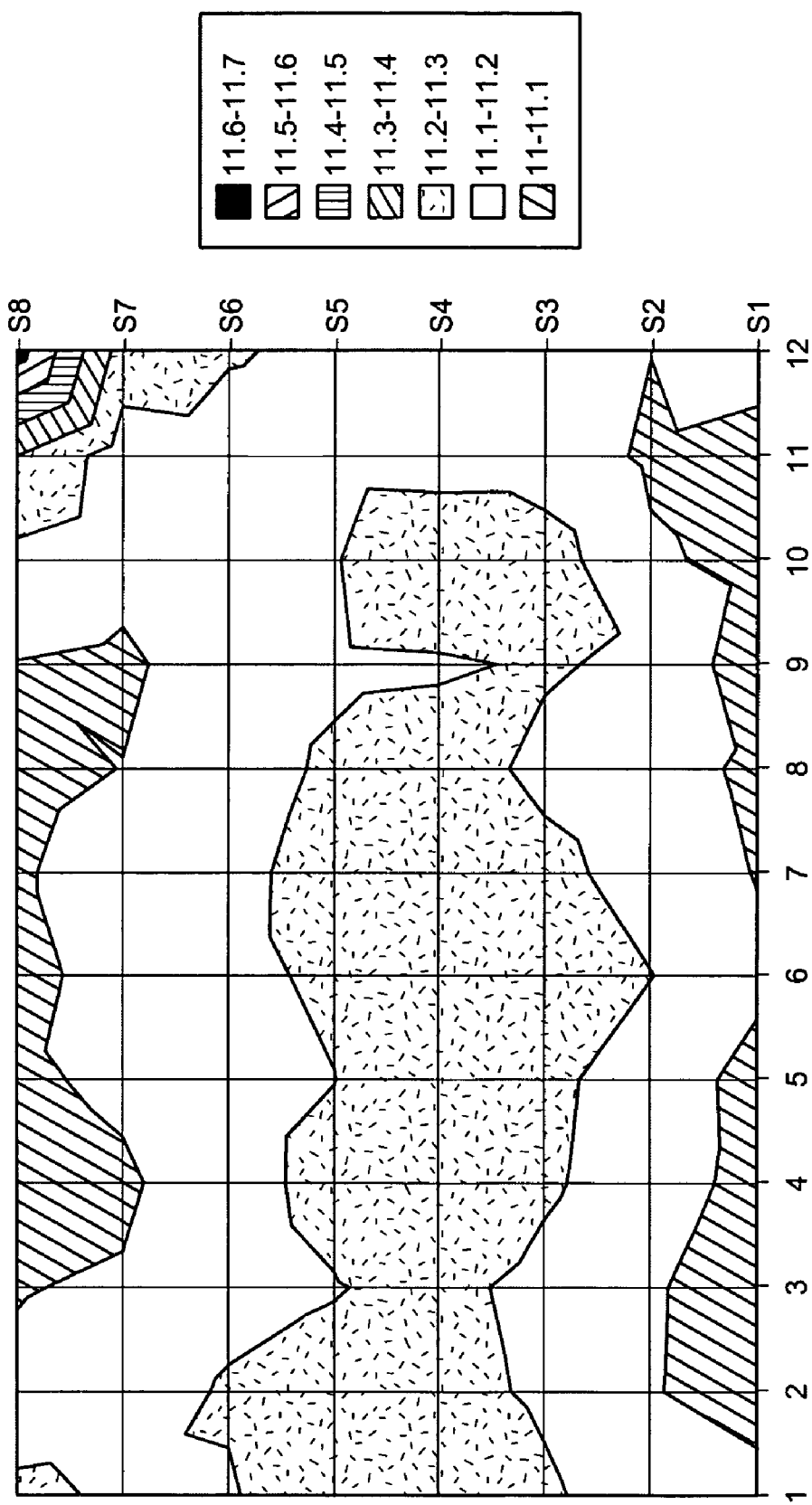
Figure 5E:
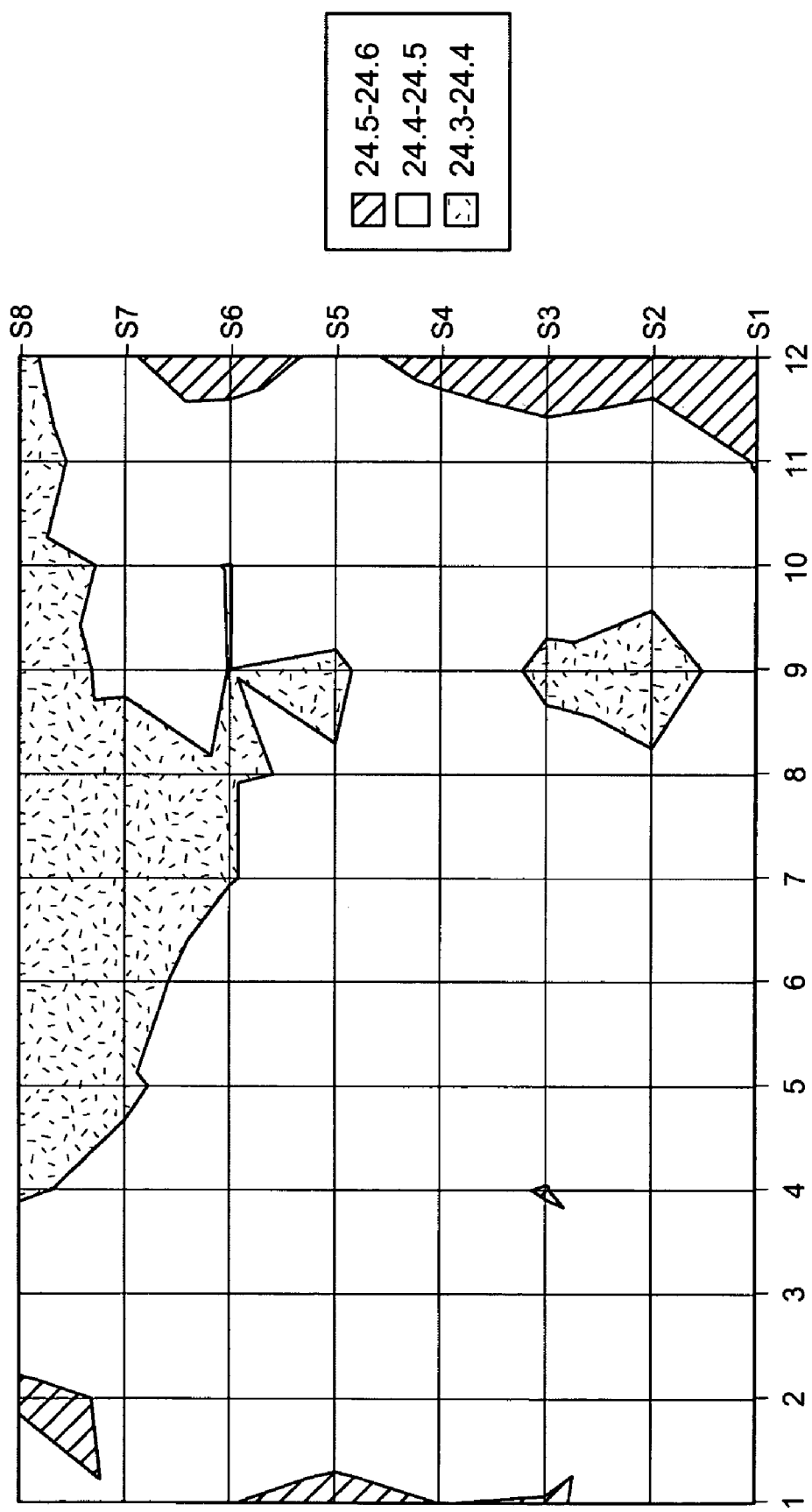
Figure 5F:
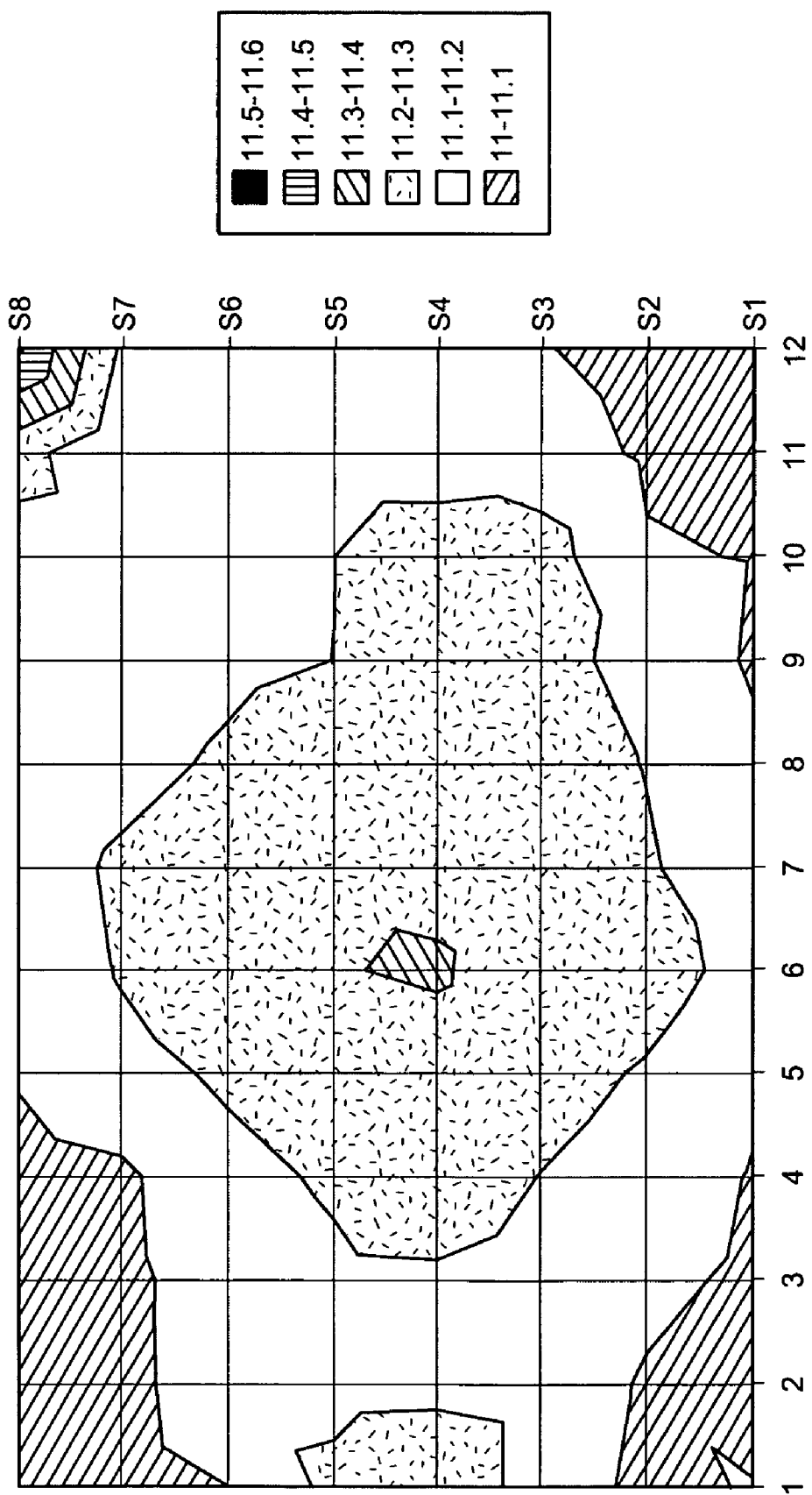

FIGS. 4A-4F illustrate the Ct values, corrections and ratios for FAM dye. The illustrations include a grid 1 to 12 and S1 to S8 representing the analysis for a 96-well tray. Other sizes for trays as known in the art can be substituted instead of a 96-well tray, including 24 wells, 384 wells, 1065 wells etc. FIG. 4A illustrates the raw data Ct values ranging from 24.3 to 25 concentration. Ct values are defined by cycles. ROX was used as a passive reference. FIG. 4B illustrates the ratio of FAM to ROX concentration to determine offset compensation ranging from −0.35 to 0.25 using the ratio of ROX with background to ROX ratio of FIG. 6. FIG. 4C illustrates converting the straight ratio of FIG. 4B into log scale to a ratio correction ranging from −0.3 to 0.3. FIG. 4D illustrates the ratio corrected Ct values ranging from 24.4 to 24.8 concentration. FIG. 4E illustrates ratio and background corrected Ct values ranging from 24.3 to 24.6 concentration. FIG. 4F illustrates corrected Ct values at cycle 40 ranging from 24.5 to 24.8 concentration. FIG. 4F illustrates plateau corrected Ct values utilizing only cycle 40 to perform the correction.

FIGS. 5A-5F illustrate the Ct values, corrections and ratios for VIC dye. The illustrations include a grid 1 to 12 and S1 to S8 representing the analysis for a 96-well tray. Other sizes for trays as known in the art can be substituted instead of a 96-well tray, including 24 wells, 384 wells, 1065 wells etc. The figures illustrate similar corrections as the FAM dye. This example for the VIC dye was not able to correct the 12-S8 well as can be seen by its variable Ct values.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a monomer" includes two or more monomers, It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A method for calibrating detection of light from biological samples comprising:
   providing a system adapted to excitation and detection of a plurality of spectrally distinguishable species, wherein the system comprises a plurality of filters;
   providing a calibration plate comprising a plurality of wells, wherein each well comprises a sample with the plurality of spectrally distinguishable species;
   detecting light from the plurality of spectrally distinguishable species for each well;
   determining a correction factor for each spectrally distinguishable species distinguished by the plurality of filters for each well.

2. The method of claim 1, wherein determining a correction factor further comprises determining a correction factor for each spectrally distinguishable species for each filter, for each well.

3. The method of claim 1, wherein each spectrally distinguishable species is associated with at least one filter of the plurality of filters.

4. The method of claim 1, wherein the plurality of spectrally distinguishable species comprises at least one dye chosen from FAM, SYBR Green, VIC, JOE, TAMRA, NED, CY-3, Texas Red, CY-5, and ROX.

5. The method of claim 1, further comprising normalizing the light detected from each well.

6. The method of claim 5, wherein the correction factor is determined prior to normalizing.

7. The method of claim 5, wherein the correction factor is determined after normalizing.

8. The method of claim 1, wherein the correction factor is determined from a plateau at the end of a run.

9. The method of claim 1, wherein the correction factor is determined from an unquenched dye at the beginning of a run.

10. The method of claim 1, wherein the correction factor is determined from log-log analysis of the run.

11. A method for calibrating detection of light from biological samples comprising:
    providing a system adapted to excitation and detection of a plurality of spectrally distinguishable species, wherein the system comprises a plurality of filters;
    providing a calibration plate comprising a plurality of wells, wherein each well comprises a sample with the plurality of spectrally distinguishable species;
    detecting light from each filter for each well;
    determining a correction factor for each filter for each well.

12. The method of claim 11, wherein determining a correction factor further comprises determining a correction factor for each spectrally distinguishable species for each filter, for each well.

13. The method of claim 11, wherein each spectrally distinguishable species is associated with at least one filter of the plurality of filters.

14. The method of claim 11, wherein the plurality of spectrally distinguishable species comprises at least one dye chosen from FAM, SYBR Green, VIC, JOE, TAMRA, NED, CY-3, Texas Red, CY-5, and ROX.

15. The method of claim 11, further comprising normalizing the light detected from each well.

16. The method of claim 15, wherein the correction factor is determined prior to normalizing.

17. The method of claim 15, wherein the correction factor is determined after normalizing.

18. The method of claim 11, wherein the correction factor is determined from a plateau at the end of a run.

19. The method of claim 11, wherein the correction factor is determined from an unquenched dye at the beginning of a run.

20. The method of claim 11, wherein the correction factor is determined from log-log analysis of the run.

* * * * *